United States Patent [19]

Barbieri

[11] 4,053,779

[45] Oct. 11, 1977

[54] METHOD AND APPARATUS FOR CONSTRUCTING MODELS OF BODY SECTIONS

[75] Inventor: Marcello Barbieri, Fulbourn, England

[73] Assignees: Robert MacMillan, Manomet, Mass.; Nicholas Della Grotta, Johnston; Guerino D. Della Grotta, Warwick, both of R.I. ; part interest to each

[21] Appl. No.: 576,109

[22] Filed: May 9, 1975

[30] Foreign Application Priority Data

May 10, 1974 United Kingdom ............... 20723/74
Nov. 8, 1974 United Kingdom ............... 48378/74

[51] Int. Cl.² .............................................. G03B 41/16
[52] U.S. Cl. .................................. 250/445 T; 250/490
[58] Field of Search ........... 250/439, 444, 445, 445 T, 250/490, 522, 523, 524, 525, 366, 368

[56] References Cited

U.S. PATENT DOCUMENTS

| 3,432,657 | 3/1969 | Slaven | 250/445 T |
| 3,549,885 | 12/1970 | Andersson | 250/522 |
| 3,778,614 | 12/1973 | Hounsfield | 250/445 T |
| 3,845,308 | 10/1974 | Cattrell | 250/522 |

Primary Examiner—Craig E. Church

[57] ABSTRACT

Two scanning systems are described to X-ray sections of a body and obtain a plurality of radiographic projections suitable for reconstruction as models of the body. The transmitted X-rays are recorded in any convenient form to produce data proportional to their intensities, and the data are converted to logarithmic form, stored and processed by a computer according to a predetermined set of original algorithms. The computer calculates a two-dimensional matrix from any set of linear arrays of data which represent the projection values of a body section. Such a matrix represents an estimate or approximation of the two dimensional distribution of the absorption or transmission coefficients of the X-rayed body section. The computer outputs are used to display pictures of the X-rayed body sections in any convenient visual or numerical form.

1 Claim, 9 Drawing Figures

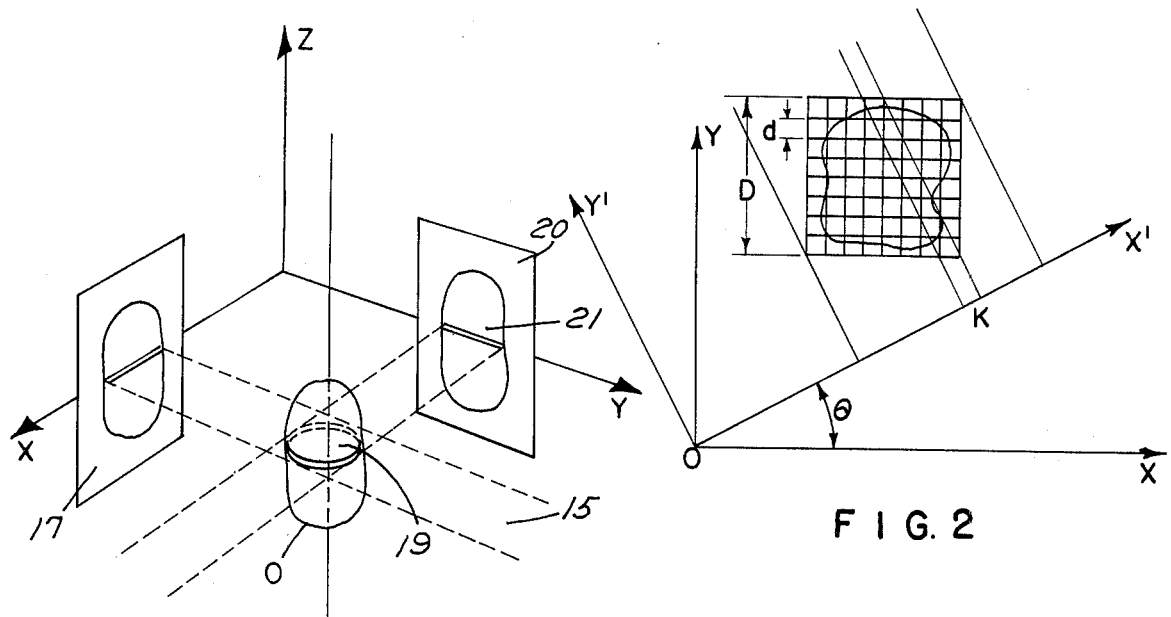
FIG. 1
FIG. 2
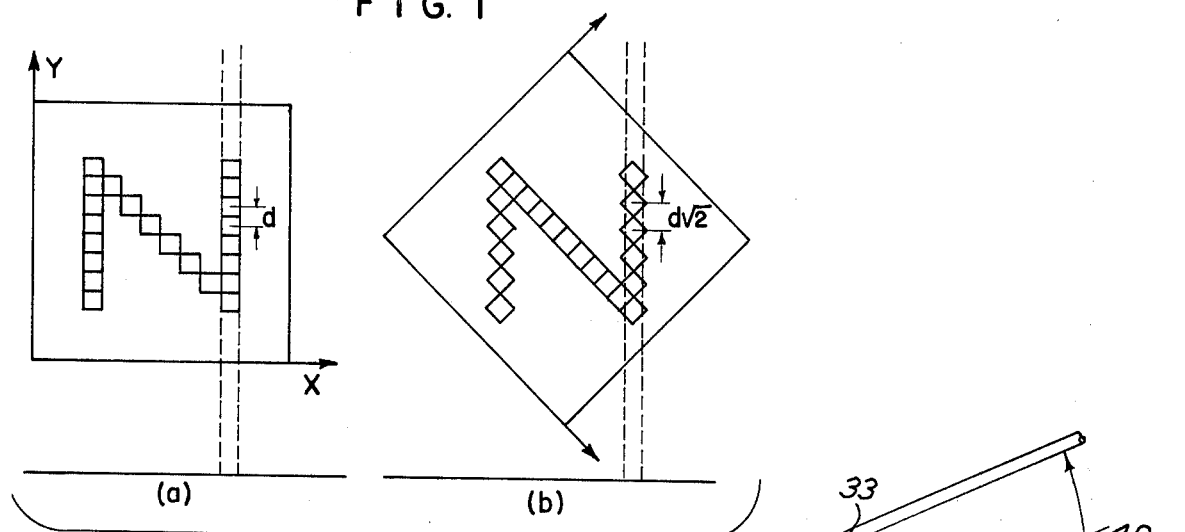
FIG. 3
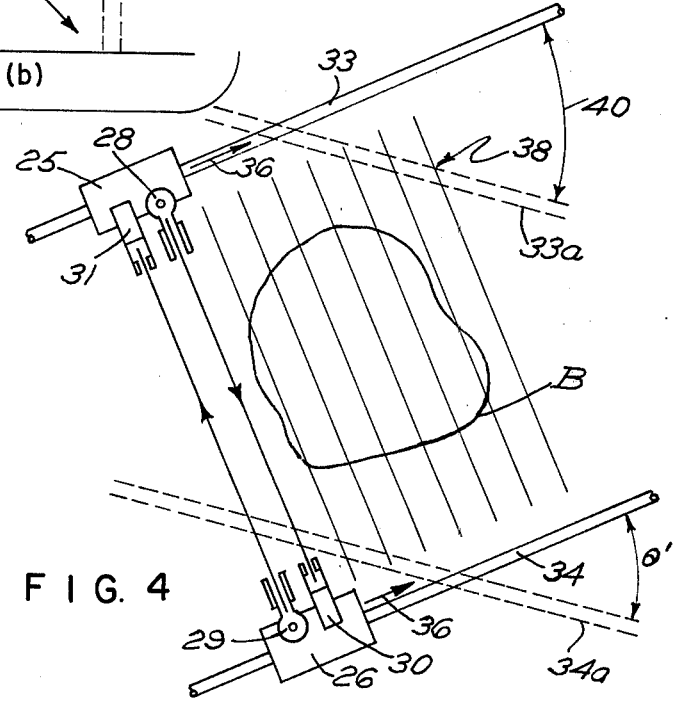
FIG. 4

METHOD AND APPARATUS FOR CONSTRUCTING MODELS OF BODY SECTIONS

BACKGROUND OF THE INVENTION

The present invention relates to the problem of reconstructing structures from X-radiographs in order to obtain, about the interior of a body, a type of information which is not evident in normal radiographs because these present two-dimensional projections of three dimensional objects, and many structural features are superimposed together on the plane of the radiographs.

It is well known that a radiograph is a two dimensional projection of a three dimensional body and many structural features of the body are superimposed onto the radiograph and are difficult to interpret. In order to distinguish superimposed features and reconstruct structures from their projections, different methods and apparatus are currently available. The oldest and most widely used radiological technique is that universally known as tomography, whose early development goes back to the 1920's, e.g. U.S. Pat. No. 3,091,692. One of the more recent developments is disclosed in U.S. Pat. No. 3,778,614, and on its basis there has been commercially produced the EMI scanner for brain research. Another is represented by the commercially available ACTA scanner, referred to in *Science*, Vol 186 (1974) page 207. Finally, a variety of methods and apparatus have been presented at the first International Workshop on Reconstruction Techniques held at Brookhaven, N.Y. from July 16 to 19, 1974, and are recorded in the Proceedings of that Congress, which have apparently not been published yet. In this specification all of the above methods and apparatus will be referred to as "the methods and apparatus presently available".

A characteristic which is common to all the scanners presently available is the low resolution of the reconstructions, and for this reason, only gross anatomical features can at present be reconstructed, and the interpretation of fine details is often impossible. The low resolution of the present scanners is due both to the limits of the experimental systems of scanning and to those of the mathematical algorithms which are used for computing the reconstructions. The present invention is dedicated to obtain substantial improvements in scanning systems and reconstruction algorithms.

SUMMARY OF THE INVENTION

The present invention describes two scanning systems for obtaining radiographic projections of a part of a body in different directions in a form which is suitable for reconstruction purposes. One of these systems (the double-beam scanner) has the aim of increasing the signal-to-noise ratio, which is the crucial limiting factor of the information needed for the reconstructions. The other (the trans-rotational scanner) has the aim of reducing the scanning time from the 4–5 minutes of the presently available apparatus to a time of the order of 10–30 seconds, with obvious advantages for what radiation protection and running costs are concerned. The two scanning systems can be used separately or integrated together into a single scanner.

In addition, the present invention describes a variety of new reconstruction operations which can be integrated together or implemented separately, which disclose a kind of information that would be otherwise irreparably lost. The present invention relates to a complete procedure, inclusive of method and apparatus, for performing reconstructions of body sections from radiographic projections. It differs from the presently available methods and apparatus by the following points:

1. All the reconstruction methods presently available, whether iterative or not, use only one reconstruction matrix. The present method uses a plurality of matrices, on the basis of the discovery that only these additional matrices disclose valuable information which would otherwise be irreparably lost.

2. All the reconstruction apparatus presently available uses only one X-ray tube. The double-beam scanning system of the present invention uses at least two X-ray tubes arranged to provide two antiparallel X-ray beams, on the basis of the discovery that such antiparallel arrangement increases the signal-to-noise ratio which is the crucial limiting factor of the information needed for the reconstructions. Antiparallel beams are directed in opposite, but parallel directions.

3. All the apparatus presently available base their reconstructions on complete projection data. The trans-rotating scanning system of the present invention provides incomplete projection data without loss of valuable information on the basis of the discovery that such arrangement reduces the scanning time from 4–5 minutes to 10–30 seconds, with obvious advantages of radiation protection and running costs.

BRIEF DESCRIPTION OF THE DRAWINGS

FIGS. 1, 2, and 3 are diagrammatic views illustrating principles of reconstruction.

FIG. 4 is a diagrammatic view of one section of scanning.

DESCRIPTION OF THE PREFERRED EMBODIMENTS

Figure 5:
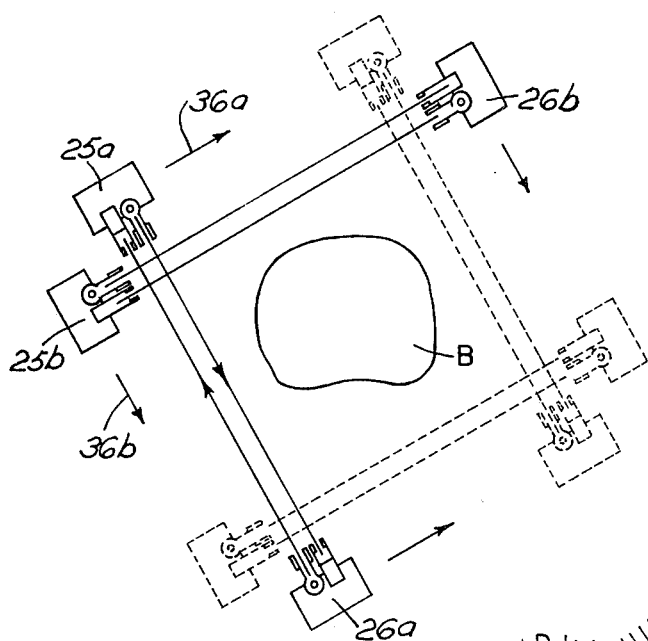
FIG. 5 is an alternate diagrammatic view of a further scanning system.

With reference to FIG. 1, when a beam 15 of X-rays which travels in direction $y$ with a uniform intensity $I_o$ crosses an object $o$ placed in its path, the transmitted and attenuated beam which emerges from the object has, in an $x$–$z$ plane 17 perpendicular to direction $y$, an intensity $I(x,y)$ described by the function $$I(x,z) = I_o e^{-\int f(x,y,z)dy} \tag{1}$$

where $f(x,y,z)$ is the attenuation coefficient of each body element $(x,y,z)$.

The transmitted intensity $I(x,z)$ is recorded by detectors which are chosen so that with a given intensity $I$, their response must be directly and linearly proportional to $I(x,z)$ and which therefore produce signals $S(x,z)$ which are described by the function $$S(x,z) = kI(x,z) \tag{2}$$

where $k$ is a proportionality constant. The integral $g(x,z)$ represents the two-dimensional projection of the three-dimensional object and is directly measurable from the recordings of the transmitted intensity. Thus $$g(x,z) = \int f(x,y,z)dy = \log I_o/I(x,z) = \log S_o/S(x,z) \tag{3}$$

where $S_o = kI$.

The reconstruction problem consists in finding the three dimensional structure $f(x,y,z)$ from a set of projections (3) obtained in different directions. This problem can be greatly simplified if the radiation scattering is negligible and if the different projections are obtained by rotating the object around an axis 18 perpendicular to the direction of the incident rays (FIG. 1). In this way, any plane of the object 19 which is perpendicular to the tilt axis is projected entirely and uniquely on a set of corresponding lines in all the different projections. For example, in FIG. 1, the projection of object 19 may be made onto plane 20 where the strip 21 is the projection. The three-dimensional reconstruction is now reduced to a set of two-dimensional reconstructions.

The following analysis is limited to the problem of reconstructing a two-dimensional section from its one-dimensional projections. A section is a region of a body contained between two ideal parallel planes whose distance is small in comparison to the size of the body. Ideally a section is regarded as infintessimally thin and therefore it is described by a two-dimensional function $f(x,y)$. As seen in FIG. 2, the projection of this function in a direction $\theta$ (or on an axis $x'$) is the one-dimensional function:

$$g(x') = \int f(x,y)dy \qquad (4)$$

with $x = x'\cos\theta - y'\sin\theta$
and $y = x'\sin\theta + y'\cos\theta$
where the projection angle $\theta$ is given by the counter-clockwise angle between the $x$ axis and an axis $x'$ perpendicular to the direction of projections (FIG. 2).

In general, however, the recording devices evaluate the projections of an object within discrete intervals which are not infintessimally thin and may be denoted $a, 2a, 3a, \ldots$ etc. and give us only a digitized set of ray sums:

$$g_{\theta K} = \int_{k - a/2}^{k + a/2} \int_{-\infty}^{\infty} f(x,y)dy'dx' \qquad (5)$$

where $k$ is a typical strip as shown in FIG. 2.

The reconstruction problem consists in finding a solution to the equations (4) and (5), which are referred to as the integral reconstruction equations.

Given a section represented by the picture $f(x,y)$, one may find a square of side length D which totally covers the picture and which may be divided into $n^2$ equal small square cells of side length $d = D/n$ (FIG. 2).

Assigning the total density of each cell to the co-ordinates $(i,j)$ of its center point, one obtains the $n$ by $n$ digitized version of the picture. That is to say, one may represent the picture itself as a $n^2$ valued matrix $f_{ij}$.

The projections of a digital picture $f_{ij}$ in a direction $\theta$ are obtained through the ray sums $$g_{\theta K} = \sum_{i=1}^{n} \sum_{j=1}^{n} a_{ij}^{\theta K} f_{ij} \qquad (6)$$

where $a_{ij}^{\theta K}$ are weighting factors which represent the fraction of the area of the cell $(i,j)$ which is contained within the ray $(\theta,K)$. The equations (6) are called the linear reconstruction equations and the algebraic version of the reconstruction problem consists in finding a solution to (6), assuming that the real ray sums given by the integrals (5) may be considered identical with the algebraic ray sums given by the equations (6).

Algebraic iterative procedures like those described in British Pat. No. 1,283,915 and U.S. Pat. No. 3,778,614 may be used to produce at each iteration a reconstruction matrix where some density values of the various cells often exceed the minimum and maximum values in the original structure. In real objects, the minimum density value possible is zero and the maximum is M. M is usually known from previous knowledge about the class of the object. For example, in biological objects, M corresponds to the density of bond. In reconstructions, negative values which are produced (values less than zero) are here called minus values, and values produced which are greater than M are here called plus values.

The production of minus and plus values during iterative algebraic reconstructions represents a spreading of density. To counterbalance this spreading, a constraint may be introduced. This means that all minus values be reset to zero and all plus values be reset to M. This operation may be repeated at any convenient time during iterations. This is a minimum procedure which allows enhancement of the reconstruction.

An improvement becomes available by the following technique. A record is kept of the occurrence and location of plus and minus values during the successive iterations. In this way, it is noticed that, while in certain cells of the reconstruction matrix the plus and minus values appear randomly, in other cells, these values always reappear after each readjustment in the previous iteration to zero and M. These cells can be called vorteces of density, more precisely negative vorteces where minus values appear and positive vorteces where plus values appear. A simple way of keeping a record of this reappearance of minus and plus values, and therefore, of the location of vorteces, is by introducing a second matrix $\mu_{ij}$. $\mu_{ij}$ is a memory matrix defined from the reconstruction matrix $f_{ij}$ in the following way:

if $f_{ij}^q \leq 0$, then $\mu_{ij}^q$ is set equal to $\mu_{ij}^{q-1} - \alpha$ if $f_{ij}^q \geq M$, then $\mu_{ij}^q$ is set equal to $\mu_{ij}^{q-1} + \alpha \qquad (7)$ otherwise $\mu_{ij}^q$ is set equal to $\mu_{ij}^{q-1}$
where $q$ is the iteration number $1,2,\ldots$ (and is not an exponent), $i$ and $j$ are the indices of the cell in the matrices, and $\alpha$ is a number used to decrement the memory matrix cells. $\alpha$ is a constant which can be chosen at will within a wide range of numbers. In particular, it is possible to set $\alpha = M$. The starting value of the reconstruction matrix, and the memory matrix, is usually the blank matrix, all cells being set to zero, but any other convenient choice may be made. Thus, normally $\mu_{ij}^0 = 0$.

After a predetermined number Q of iterations, a cell $(i,j)$ is said to be a positive or a negative vortex if $\mu_{ij}^Q \geq X$ or if $\mu_{ij}^Q \leq -X$, where $X \leq q\alpha$. Where density vorteces are found, a new kind of information is obtained. The density values of these points no longer need to be treated as free unknowns in the reconstruction, but may be fixed to zero or M, according to whether they are negative or positive vorteces, and they may be erased from the list of unknowns in the reconstruction matrix. In this way, the memory matrix permits one to identify vorteces. By fixing these points and excluding them in subsequent iterations, on progressively reduces the number of unknowns while keeping constant the number of reconstruction equations. This clearly permits a more rapid and more exact solution as the ratio of equations to unknowns is steadily increased. This technique is called density modulation.

A more general operation is also possible with the help of the memory matrix. Let a reservoir matrix be used to store the values $f_{ij}{}^q$ before they are converted into $f_{ij}{}^{q+1}$ by the algorithm. In this expression, $(q+1)$ is the term indicating the next iteration. In this way, the increments $f_{ij}{}^{q+1} - f_{ij}{}^q$ may be calculated, and after each iteration, one may set $$\mu_{ij}{}^{q+1} \text{ equal to } \mu_{ij}{}^q + |f_{ij}{}^{q+1} - f_{ij}{}^q| \tag{8}$$

(where $|\ldots|$ indicates an absolute value)

After a certain number Q of iterations (for example, 5), one may examine the value of the cell $(i,j)$ of matrix $\mu_{ij}{}^Q$, and if the resulting value is smaller than some predetermined quantity $\epsilon$, (where $\epsilon$ may be chosen in any convenient way fixed by experience), it is obvious that all of the readjustments of the reconstruction matrix have had no significant effect on the cell $(i,j)$ in the matrix $f_{ij}$. Such cells are called stationary, and, as with the density vorteces, these too may be fixed, in this case to their last value, and erased from the list of unknowns.

A combined way of utilizing the memory matrix to recognize both the density vorteces and the stationary point is the following: Referring to FIG. 2, given a ray $(\theta,K)$, let $N_{\theta K}{}^O$, $N_{\theta K}{}^M$, and $N_{\theta K}{}^S$ indicates respectively the number of negative vorteces, positive vorteces and stationary poins which fall within this ray. Let $g_{\theta K}$ and $g_{\theta K}{}^q$ be the ray sums of the original structure and of the reconstructed matrix (at the $q$th iteration) respectively. Let us indicate in the memory matrix the negative vorteces as $V_o$, positive vorteces as $V_M$, and stationary points as $S$. At each iteration, the reconstruction matrix is readjusted according to the following expressions:

$$\text{if } \mu_{ij}^q = V_o, \text{ or if } \mu_{ij}^q = V_M, \text{ or if } \mu_{ij}^q = S, \text{ then} \tag{9}$$

$$f_{ij}^{q+1} \text{ is set equal to } f_{ij}^q$$

otherwise, $f_{ij}{}^{q+1}$ is set equal to $f_{ij}{}^q +$ $$\frac{g_{\theta K} - g_{\theta K}{}^q}{N_{\theta K} - (N_{\theta K}{}^O + N_{\theta K}{}^M + N_{\theta K}{}^S)}$$

In addition to the reconstruction matrix, the memory matrix is also readjusted at each iteration, and this is done for each cell of the matrix with the following scheme:

if $\mu_{ij}^q = V_O$, or if $\mu_{ij}^q = V_M$, or if $\mu_{ij}^q = S$, then
$\mu_{ij}^{q+1} = \mu_{ij}^q$ if $f_{ij}^{q+1} \leq 0$ and $\mu_{ij}^q \neq V_O$, then $\mu_{ij}^{q+1} = \mu_{ij}^q + M$ if $f_{ij}^{q+1} \geq M$ and $\mu_{ij}^q \neq V_M$, then $\mu_{ij}^{q+1} \mu_{ij}^q + M$ (10)

otherwise $\mu_{ij}^{q+1} = \mu_{ij}^q + |f_{ij}^{q+1} - f_{ij}^q|$

The definition of the density vorteces and the stationary points is performed periodically, after a cycle Q of iterations, and may be done through the following expressions:

if $\mu_{ij}^Q = V_O$, or $\mu_{ij}^Q = V_M$, or $\mu_{ij}^Q = S$, then $\mu_{ij}^{Q+1} = \mu_{ij}^Q$ if $\mu_{ij}^Q \leq -X$, then $\mu_{ij}^{Q+1} = V_O$ and $f_{ij}^{Q+1} = 0$ if $\mu_{ij}^Q \geq +X$, then $\mu_{ij}^{Q+1} = V_M$ and $f_{ij}^{Q+1} = M$ if $0 \leq \mu_{ij}^Q \leq \epsilon$, then $\mu_{ij}^{Q+1} = S$ (11)

otherwise $\mu_{ij}^{Q+1} = 0$

It is obvious that the original number of unknowns is N, where $N = \Sigma_K N_{\theta K}$, while, after the recognition of the density vorteces and the stationary points, it becomes $$N' = \sum_K (N_{\theta K} - N_{\theta K}{}^O - N_{\theta K}{}^M - N_{\theta K}{}^S),$$

whereas the number of equations remains constantly to $\Sigma_\theta \Sigma_K g_{\theta K}$.

Expressions (2), (3) and (4) become a complete reconstruction algorithm when the values of M and Q, together with those of the starting matrix $f_{ij}$ are specified. The starting matrix $f_{ij}{}^o$ is usually the blank matrix $f_{ij} = 0$, but any other convenient choice may be made. The maximum density value M corresponds to the absorbtion or transmission coefficient of the densest component of the examined object, which, for biological bodies, is usually the bone.

The value of Q can, in general, be set to 5, but, because density modulation is a picture-dependent algorithm, the best specification is usually obtained by preliminary trials on a prototype of the class of objects which have to be reconstructed. The reconstruction algorithm obtained in this way is referred to as density modulation reconstruction technique.

The specification of the projection angles requires the choice of a reference system, an operation which is highly arbitrary and which, in practice, affects all the iterative reconstruction algorithms.

Consider, for example, the picture of FIG. 3 which is contained in two matrices rotated at 45° with respect to each other. The projection of the external bar of the picture is distributed in FIG. 3a within a ray of length L whose center points have a distance $d$, whereas in FIG. 3b the same projection is distributed within a ray of different length and between cells whose distance are $d\sqrt{2}$.

The choice of different reference systems should not interfere with the result of a reconstruction, but in practice this does happen, and we may try to counterbalance this effect by a convenient constraint which is called isotropic weighting because its aim is precisely that of reducing the anisotropy produced by an arbitrary reference system. We may implement this constraint by performing separate reconstructions with differently oriented matrices $f_{ij}{}^o$ and $f_{zw}{}^\xi$ where the index $\xi$ means that the projections are regarded as tilted at an angle $\xi$ with respect to an original orientation characterized by the index 0. In practice, the reconstructions of two matrices are often sufficient, and in this case, the second set is taken at 45° with respect to the first one.

Given a set of projection values $g_{\theta K}$, we obtain from it two sets of data $g_{\theta K}{}^O$ and $g_{(\theta + \xi), K}$ to which two parallel reconstruction processes are applied.

In order to introduce the constraint, the two matrices are translated one over the other until their two centers coincide, while their relative orientation is kept constant. Then we define the function $\delta(z, w \in i,j)$ where $\in$ means "belonging to", as 1 if the center point $(z,w)$ of one matrix falls within the area of the cell of the other matrix whose center point is $(i,j)$ and zero elsewhere. After that, the isotropic weighted matrix is obtained through the operation $$[f_{ij}{}^0 + f_{zw}{}^\xi \delta(z, w \in i, j)] \quad (16)$$

and the expression (16) may be applied at any convenient stage of an iterative reconstruction process.

It will be appreciated that the errors due to the arbitrary choices of the reference system are classical examples of digitization noise, and the use of the isotropic weighting constraint is a powerful way of decreasing this noise.

Given a picture represented by a matrix $f_{ij}$, define as a complementary picture a matrix $f_{ij}{}^C$ such that $$f_{ij} + f_{ij}{}^C = \Omega_O \quad (19)$$

where $\Omega_O$ represents a constant matrix with density values $$\omega_{ij} = f_{ij} + f_{ij}{}^C \quad (20)$$

Given the projection values $g_{\theta K}$ of a picture, one may obtain the projection values of a complementary picture with the expressions $$g_{\theta K}{}^C [\sum_i \sum_j \alpha_{ij}{}^{\theta K}{}_{ij} \omega_O \delta(i, j \in \theta K)] - g_{\theta K} \quad (21)$$

where $\omega_O$ may be selected in any convenient way to assure that $$\omega_O \geq \max(f_{ij})$$

so that no value of the complementary matrix turns out to be negative.

The sum of a picture and a corresponding complementary picture is called the omega-matrix of the given picture, and, from the definition itself of complementary matrix, it follows that if the two parallel reconstructions of a picture and a complementary picture are carried out from their projection values, the resulting reconstructed omega-matrix should always be a constant one.

This reconstruction property is referred to as the omega-matrix uniformity constraint, and it is obvious that if the projection values of the complementary matrix are calculated from expressions (21) and all the reconstruction operations are linear, this constraint is always respected.

However, even simple and obvious reconstruction constraints, such as the requirement that no density value be negative, necessarily require the use of non-linear operations and this affects the reconstruction of any pair of complementary matrices, introducing discontinuities in their omega-matrix.

On the other hand, omega-matrix uniformity may always be regarded as a requirement which should be fulfilled by a correct reconstruction procedure and the omega-matrix discontinuities may be corrected by the following equations. Given three reconstructed matrices $f_{ij}, f_{ij}{}^C$ and $\omega_{ij}$ with $f_{ij} + f_{ij}{}^C = \omega_{ij} \neq \omega_O$, then set $$\bar{f}_{ij} = f_{ij} + \frac{1}{2}(\omega_o - \omega_{ij}) \quad (22)$$

and $$\bar{f}_{ij}{}^C = f_{ij}{}^C + \frac{1}{2}(\omega_o - \omega_{ij}) \quad (23)$$

so that $$\bar{f}_{ij} + \bar{f}_{ij}{}^C = \omega_{ij} = \omega_o \quad (24)$$

This simple way of utilizing the omega-matrix information makes it possible to satisfy the omega-matrix uniformity constraint while still using any desired set of non-linear reconstruction operations, and it has been found of great value for reconstruction purposes.

Referring now to FIG. 4 of the drawings, there is illustrated herein one principle of scanning in accordance with the invention. The scanning unit for examining the body B is composed of a pair of holders or frame like members 25 and 26, each of which carries respectively an X-ray source 28, a detector 31 and an X-ray source 29 and a detector 30. The arrangement is such that each of these holders 25 and 26 orient their respective sources and detectors in such a way that the X-ray source 28 is directed toward its detector 30 and the X-ray source 29 is directed toward its detector 31. On parallel lines, it is desirable that the X-ray sources 28 and 29 produce beams of small cross sectional area, preferably no larger than 3 square millimeters, and preferably includes a collimator which reduces the scatter of the X-rays. The detector should also include a collimator and may take the form of a scintillator. the holders 25 and 26 are mounted for movement on parallel rails which are shown diagrammatically as 33 and 34 respectively which maintain the sources at a constant distance apart and means which are not shown are used to move the holders 25 and 26 at a convenient speed in the direction shown by the arrows 36 and 36'. In this fashion, the scanning units are moved over a length necessary to examine the body B and a convenient number of transmissions from the X-ray sources 28 and 29 are made which are represented by the parallel lines generally designated 38, the number of which is purely exemplary and is not intended to be limiting. It will be apparent that as the holders 25 and 26 move and scan the body B, in effect the X-ray beams generated from the sources 28 and 29 will pass through the same line of the object after a certain interval of time which we could call the superimposition time which depends upon the velocity of translation and the distance which separates the X-ray source and the detector in each one of the holders. The two projection values that are obtained in this way for each ray path through the object may then be added together and their averages taken as the projection value of the ray.

This type of scanning has certain fundamental characteristics which should be appreciated. The two antiparallel X-ray beams which cross the same path of the object in opposite directions should ideally produce identical projection values. In practice, however, the physical extension of the X-ray source, the imperfect parallelism of any collimating system, the anisotropy of the X-ray scattering and many sources of statistical noise alway produce different, even if equally representative, results. The sum, however, of the projection values obtained by the two antiparallel beams reinforces the part of the signal which comes from real structural features and decreases by the averaging situation that which is due to statistical, anisotropic and geometrical kinds of noise, producing an overall increase in the signal-to-noise ratio which is the real critical factor of the scanning system. In addition, the fact that the two antiparallel X-ray beams scan the same paths through the object after a finite superimposition time which in practice is a fraction of a second is helpful in examining organs that are in movement, such as the heart, since the sum of the projections of the two configurations which succeed each other after the superimposition time makes the averaged projection independent of the conformational changes which occur within the superimposition time.

From a practical standpoint, it is desirable to make more than one path across the scanned object B, and to this end the rails 33 and 34 in the associated mechanical apparatus (not shown) which move the holders 25 and 26 therealong are rotated relative to the body B as indicated by the arrow 40 at a second convenient angle so that they will lie as shown by the dotted lines designated 33a and 34a and in this position the scanning is repeated to collect projection at a different angle which we shall call $\theta'$. In this way there is a basic advantage to using this particular type of apparatus which uses not only more than one X-ray beam, but also can rotate the same about the body section to be examined.

The general considerations of examining a body B lead to extending the basic scheme illustrated in FIG. 4 and to this end, reference is made to FIG. 5, where there is illustrated in simple fashion an apparatus which makes use of at least two orthogonal scanning units 25a, 26a, 25b and 26b which can simultaneously move as indicated by the arrows 36a and 36b and simultaneously collect two sets of data.

Figure 6:
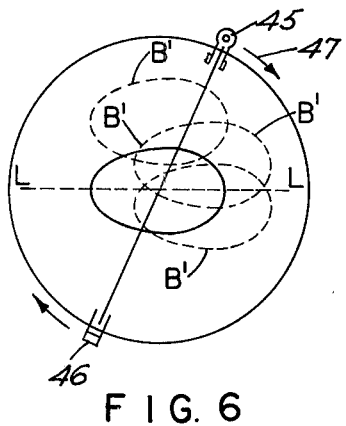
FIGS. 6 and 6A are alternate systems.
Figure 7:
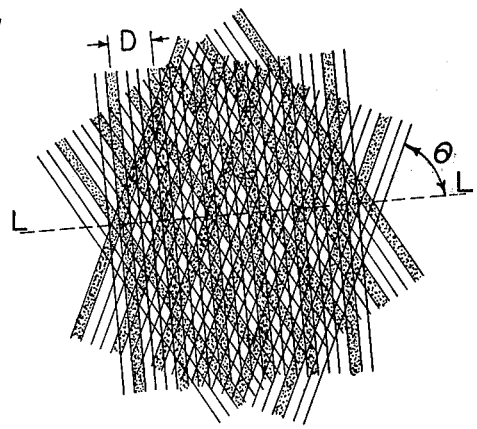
FIG. 7 is a diagrammatic view illustrating the scanning system of FIG. 6.

A second embodiment of the invention will be seen by reference to FIG. 6 of the drawings, where there is disclosed an X-ray source 45 and a detector 46 which are arranged to perform a circular scan about body B' as indicated by the arrow 47. The body B' and the arrangement of the X-ray source and its detector are set to provide relative motion, the body B', for example, moving relative to the rotating X-ray source and scanner on a line L to several positions, one of which is indicated by the dotted lines. To understand how this particular apparatus would operate, reference should be had to FIG. 7. Here it can be appreciated by referring to the shaded areas that after a complete revolution, the X-ray beam would return to scan the object at the same angle, but only after the object has shifted by a length D, which will depend entirely on the translational speed of the body under examination and the scanning frame. In this case, therefore, any projection at an angle is incomplete because the projection values are recorded not for all of the paths which cross the object at the angle $\theta$, but only for those paths which are separated by a distance D along the direction of the translation line LL. It is obvious, however, thhat with a rotating scanning unit, the minimum angle between the directions of the two distinct projections can be very small, and therefore, even if each projection gives a reduced set of data, the number of distinct projection angles can be increased practically at will. The total number of reconstruction equations of a scanner of this nature is disclosed in FIG. 6 and can easily be equalled to that of a conventional scanner so long as the projection data collected at each angle is compensated for by an increase in the number of projection angles. In any event, when the projections at different angles are superimposed together as illustrated in FIG. 7, the whole reconstruction region can be completely covered with incomplete projections, provided enough angles of data collection are used.

This type of scanner has certain advantages when it is operated in the proper fashion. Assume that rotation is performed in one second and that the translational speed of the body relative to the scanner center denoted by the letter C is one centimeter per second. It becomes obvious that the scanning of an object whose width is 20 centimeters requires 20 seconds.

Figure 8:
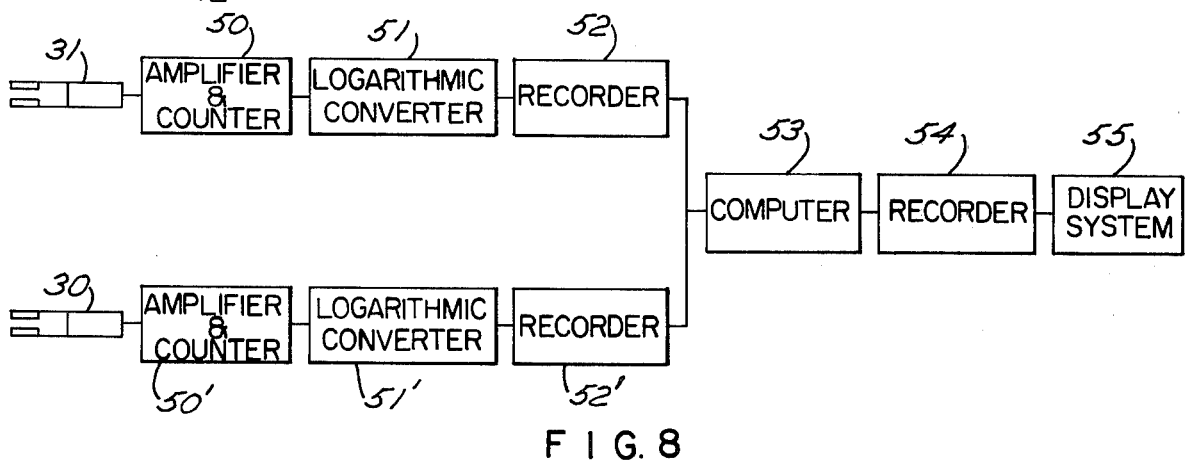
FIG. 8 is a diagrammatic view in block form illustrating the apparatus used.

FIG. 8 shows a block diagram of an apparatus for producing pictures from the signals registered from the detectors and particularly the apparatus illustrated in FIG. 4, and which is also applicable to that illustrated in FIG. 6. The outputs the detectors 30 and 31 are applied to amplifier and counters 50 and 50' respectively which will produce a digital output representing the number of counts in each reading. The output of these devices are then applied to a logarithmic converter 51 and 51' which gives a logarithmic transformation and the output of this is then fed into a punched tape, magnetic tape or disc recorder 52 and 52'. The output from the recorders are then fed to computer 53, which performs three types of operations on the digitized projection values stored in the recorder 52 and 52'. The first operation consists in the precise indexing of the projection values to add together all of the values produced by the antiparallel beams which pass through the same path of the examined object. The second operation consists of applying to the projection data a reconstruction procedure according to that described above and the third operation consists of applying to the reconstructed pictures any convenient processing for obtaining a visual display which can be easily examined that takes advantage of all of the procedures for picture restoration and picture enhancement which are universally known from the scientific literature and which are usually implemented with fast Fourier transforms. After the computer processing, the reconstructed and restored and enhanced picture may be stored in a recorder 54, which may include a digital-to-analog converter, and then may be applied directed to a display system 55, which provides a visual representation of the reconstructed picture in any convenient form, such as a visual pattern on a cathode-ray tube, or as a photograph, or as a printed map of the reconstructed attenuation coefficients in the examined section. The apparatus described in FIG. 6, where an X-ray source describes a rotation around an object while the object in translated along a line may appear similar to that described in the U.S. Pat. No. 3,106,640 to Oldendorf. However, there are basic differences between the two. In the Oldendorf apparatus, the radiation intensities transmitted through linear paths which intersect a given point are used to describe the radiodensity of that and only that point. The description of the entire object results then from repeating the same procedure for all the points of interest. It is clear that this is a mere tomographic description of the object in which the principle of selective blurring and enhancement is not used plane by plane as in conventional apparatus but point by point. In the present apparatus, such an approach is abandoned because of the intrinsic limitations of any tomographic procedure. In the present invention, the description of any point of the examined structure does not come only from the rays which intersect that point but also from all other rays which cross the object. For this reason, from the disclosed device, the data must be further processed by a reconstruction algorithm which is absent in the Ohlendorf patent, and in this respect, the difference between the method disclosed herein and the Ohlendorf method is similar to that between U.S. Pat. No. 3,778,614 of EMI and Ohlendorf U.S. Pat. No. 3,106,640.

FIG. 6 illustrates a scanning system where the X-ray source rotates around an object while the object is translated along a line. However, the principle of the invention can be carried out even with an object that is subjected to kinds of motion other than translation. For example, while circular, elliptical or spiraloid motion and many alternative movements can be performed, the circular motion of the X-ray source continues to hold good. The displacements of the body B might well not follow a straight path.

Figure 6A:
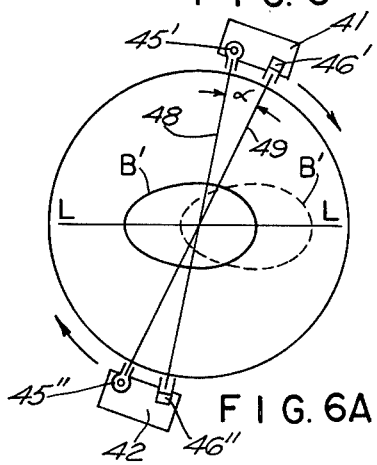

Referring now to FIG. 6A of the drawings, there is illustrated herein another system in accordance with the invention which is still based on the principle of the double beam scanning. The scanning unit for examining the body B' is composed of a pair of holders of frame-like members 41, 42, each of which carries respectively an X-ray source 45° and a detector 46' and an X-ray source 45'' and a detector 46''. The arrangement is such that each of these holders 41, 42 orient their respective sources and detectors in such a way that the X-ray source 45' produces a beam 48 directed towards the detector 46'' and the X-ray source 45'' produces a beam 49 directed towards the detector 46'. It is desirable that the X-ray sources 45' and 45'' produce beams of small cross sectional area, preferably no larger than 2 square millimeters, and preferably include collimators which reduce the scattering of the X-rays. The detectors 46' and 46'' should also include a collimator and may take the form of scintillators. The X-ray source and detectors are arranged so that their X-ray beams form an angle $\alpha$ and intersect at a point $c$. The holders 41, 42 are arranged to perform a circular scan around the center $c$ with an angular speed $\omega$ as indicated by the arrow 47. During the scan, the body B' can be held stationary or can be translated at a speed V on a line L to several positions, one of which is indicated by the dotted lines. The time necessary to scan the angle $\alpha$ at the selected angular speed is called the superimposition time because the X-ray beam 48 crosses the object at a time $t_2$ at the same angle at which the beam 49 was crossing the object at a time $t_1$, where $t_2 - t_1$ represent the superimposition time. If the object is held stationary, the beams 48, 49 would cross the same path of the object (in opposite directions) after the superimposition time.

If the object is translated at a speed V, the centers of the paths scanned by the two beams after the superimposition would be shifted apart. It will be appreciated, however, that if the speed V is conveniently slow, this shift can be made small enough to allow a considerable overlapping of the two said paths, and the signals of the beams 48, 49 taken after the superimposition time are representative of the overlapped region of the two scanned objects' paths. In this way the principle of double beam scanning continues to hold good for the apparatus illustrated in FIG. 5.

This apparatus, the rotating double beam scanner, has characteristics which may make it convenient in certain practical instances. For example, if the reconstructions are performed for regions of the body where organs perform periodical movements (for example the heart) it is possible to vary the angular speed $\omega$ of the rotating unit in any convenient way which is related to the period of the motion of these organs as detected by usual means like an electrocardiogram. In this way it is possible to group in different classes the projections which correspond to different phases of the selected organ movement. For example, it is possible to discriminate between the projections taken during the systole and those taken during the diastole and perform separate reconstructions for the same body section at these two different stages.

Note that three distinct reconstruction operations have been disclosed. One of these is a complete algorithm, called density modulation. The other two operations are reconstruction constraints, that is, operations which are not in themselves algorithms, but which can be introduced into an algorithm to improve it. These constraints are isotropic weighting and omega matrix uniformity.

What is claimed is:

1. Apparatus for examining a body using radiation having a wavelength between 0.1A and 159A, comprising:
    A. a first source of radiation disposed to transmit radiation through a body and a first detecting means for detecting radiation from said first source transmitted through said body,
    B. a second radiation source adjacent said first detector for transmitting radiation through a body to be examined and second detecting means adjacent said first radiation source for detecting radiation from said second source transmitted through said body,
    C. means for translating said sources and detectors simultaneously across a section of the body,
    D. means for controlling the sources to generate a plurality of successive rays,
    E. each detecting means generating an output corresponding to the image of the body between the radiation source and the detecting means,
    E. circuit means for summing the outputs of said detectors,
    F. circuit means for processing the resultant signal to obtain an output, and
    G. means responsive to said output for producing a visual representation.

* * * * *